United States Patent
Fujii et al.

(10) Patent No.: US 11,442,036 B2
(45) Date of Patent: Sep. 13, 2022

(54) SENSOR ELEMENT AND GAS SENSOR

(71) Applicant: NGK INSULATORS, LTD., Aichi (JP)

(72) Inventors: Yusuke Fujii, Nagoya (JP); Sang Jae Lee, Oberursel (DE)

(73) Assignee: NGK INSULATORS, LTD., Nagoya (JP)

( * ) Notice: Subject to any disclaimer, the term of this patent is extended or adjusted under 35 U.S.C. 154(b) by 843 days.

(21) Appl. No.: 16/243,120

(22) Filed: Jan. 9, 2019

(65) Prior Publication Data

US 2019/0145925 A1  May 16, 2019

Related U.S. Application Data

(63) Continuation of application No. PCT/JP2018/022910, filed on Jun. 15, 2018.

(30) Foreign Application Priority Data

Jun. 16, 2017  (JP) .............................. JP2017-118937

(51) Int. Cl.
| | |
|---|---|
| *G01N 27/407* | (2006.01) |
| *G01N 27/406* | (2006.01) |
| *G01N 33/00* | (2006.01) |
| *G01N 27/416* | (2006.01) |
| *G01N 27/419* | (2006.01) |

(52) U.S. Cl.
CPC ..... *G01N 27/4078* (2013.01); *G01N 27/4062* (2013.01); *G01N 27/416* (2013.01); *G01N 27/419* (2013.01); *G01N 33/0037* (2013.01)

(58) Field of Classification Search
CPC ........... G01N 27/4078; G01N 27/4062; G01N 27/416; G01N 27/419; G01N 33/0037; Y02A 50/20
See application file for complete search history.

(56) References Cited

U.S. PATENT DOCUMENTS

| | | |
|---|---|---|
| 2001/0008211 A1 | 7/2001 | Kato et al. |
| 2007/0084723 A1 | 4/2007 | Soken |
| 2010/0006433 A1 | 1/2010 | Yasuda et al. |
| 2012/0217160 A1 | 8/2012 | Hayashi et al. |

(Continued)

FOREIGN PATENT DOCUMENTS

| | | | | |
|---|---|---|---|---|
| EP | 0 798 556 A2 | 10/1997 | | |
| EP | 0798556 B1 * | 8/2003 | ........... | G01N 27/417 |

(Continued)

OTHER PUBLICATIONS

Nakagaki et al. (JP 2006284223 a, machine translation) (Year: 2006).*

(Continued)

*Primary Examiner* — Joshua L Allen
(74) *Attorney, Agent, or Firm* — Mattingly & Malur, PC

(57) ABSTRACT

A sensor element includes an element main body in which a flow portion of a measurement-object gas is disposed, a measurement electrode disposed in the flow portion of a measurement-object gas, a measurement electrode lead having a first portion that is connected to the measurement electrode and that is disposed in the flow portion of a measurement-object gas and a second portion that is connected to the first portion and that is embedded in the element main body, a hermetic layer that is part of the element main body and that surrounds an end region of the second portion including the border with the first portion; and a lead insulating layer that is part of the element main body and that surrounds at least part of the second portion excluding the end region.

4 Claims, 3 Drawing Sheets

(56) References Cited

U.S. PATENT DOCUMENTS

| | | | |
|---|---|---|---|
| 2014/0190828 A1* | 7/2014 | Kamada | G01N 27/4078 |
| | | | 204/427 |
| 2015/0253281 A1* | 9/2015 | Saito | G01N 27/409 |
| | | | 204/416 |
| 2015/0268187 A1 | 9/2015 | Adachi et al. | |
| 2015/0276657 A1* | 10/2015 | Sekiya | G01N 27/4072 |
| | | | 204/424 |

FOREIGN PATENT DOCUMENTS

| | | | |
|---|---|---|---|
| JP | 10-267893 A | | 10/1998 |
| JP | 2006284223 A | * | 10/2006 |
| JP | 2010-038904 A | | 2/2010 |
| JP | 2012-177638 A | | 9/2012 |
| JP | 2015-178988 A | | 10/2015 |
| JP | 2015-180867 A | | 10/2015 |
| JP | 2015-227896 A | | 12/2015 |
| WO | 2018/016604 A1 | | 1/2018 |

OTHER PUBLICATIONS

International Search Report of PCT/JP2018/022910 dated Sep. 18, 2018.

Chinese Office Action received in corresponding Chinese Application No. 201880002775.9 dated Oct. 11, 2021.

International Preliminary Report on Patentability received in corresponding International Application No. PCT/JP2018/022910 dated Dec. 26, 2019.

Chinese Office Action received in corresponding Chinese Application No. 201880002775.9 dated Jun. 9, 2022.

* cited by examiner

SENSOR ELEMENT AND GAS SENSOR

CROSS-REFERENCE TO RELATED APPLICATION

This application is a continuation application of PCT/JP2018/022910, filed on Jun. 15, 2018, which claims the benefit of priority from Japanese Patent Application No. 2017-118937, filed on Jun. 16, 2017, the entire contents of which are incorporated herein by reference.

BACKGROUND OF THE INVENTION

1. Field of the Invention

The present invention relates to a sensor element and a gas sensor.

2. Description of the Related Art

To date, sensor elements that detect specific gas concentrations of NOx and the like in gases to be measured, for example, an automobile exhaust gas, have been known (for example, PTL 1). A sensor element described in PTL 1 includes a plurality of solid electrolyte bodies stacked, a plurality of electrodes arranged in internal spaces of the solid electrolyte bodies, leads connected to respective electrodes, and insulating layers that insulate leads. The insulating layer is disposed on the surface of the solid electrolyte body, and the lead is disposed on the insulating layer. Consequently, the insulating layer insulates the lead from the solid electrolyte body. Alumina is described as the material for forming the insulating layer. This sensor element decomposes NOx in an exhaust gas into nitrogen and oxygen on the electrodes and detects a NOx concentration on the basis of a current that flows between the electrodes because of the resulting oxygen.

CITATION LIST

Patent Literature

PTL 1: JP 2015-227896 A

SUMMARY OF THE INVENTION

In this regard, the insulating layer that insulates the lead may be a member such as a porous body that passes oxygen. Consequently, if paths through which oxygen reaches the insulating layer from the outside are present due to, for example, fine spaces generated during production of the sensor element, cracks after production, and the like, oxygen may reach an electrode connected to the lead through the paths or the insulating layer. Then, if oxygen that does not derived from a specific gas reaches the electrode, as described above, the detection accuracy of the specific gas concentration may be degraded.

The present invention was realized so as to address such a problem, and it is a main object of the present invention to suppress degradation of the detection accuracy of the specific gas concentration.

In order to achieve the above-described object, the present invention adopts the following configuration.

A sensor element according to the present invention includes an element main body which has a plurality of oxygen-ion-conductive solid electrolyte layers stacked and in which a flow portion of a measurement-object gas is disposed so as to introduce and pass the measurement-object gas, a measurement electrode disposed in the flow portion of a measurement-object gas, a measurement electrode lead having a first portion that is connected to the measurement electrode and that is disposed in the flow portion of a measurement-object gas and a second portion that is connected to the first portion and that is embedded in the element main body, a hermetic layer that is part of the element main body and that surrounds an end region of the second portion including the border with the first portion, and a lead insulating layer that is part of the element main body and that surrounds at least part of the second portion excluding the end region.

In the sensor element, the measurement electrode lead has the first portion that is disposed in the flow portion of a measurement-object gas and the second portion that is connected to the first portion and that is embedded in the element main body. In addition, the hermetic layer surrounds the end region of the second portion including the border with the first portion, and the lead insulating layer surrounds at least part of the second portion excluding the end region. Consequently, even when oxygen reaches the lead insulating layer from the outside and oxygen moves in the lead insulating layer, oxygen in the lead insulating layer does not readily reach the flow portion of a measurement-object gas because the end region that serves as an outlet to the flow portion of a measurement-object gas in the second portion is surrounded by the hermetic layer. As a result, degradation of the detection accuracy of the specific gas concentration due to oxygen reaching the measurement electrode from the outside can be suppressed.

In this regard, the porosity of the hermetic layer may be 0% by volume or more and 2% by volume or less. Preferably, the measurement electrode lead is hermetic. The porosity of the measurement electrode lead may be 0% by volume or more and 10% by volume or less. The porosity of the measurement electrode lead is preferably less than 5% by volume and more preferably 2% by volume or less. The lead insulating layer has higher oxygen permeability than the hermetic layer. The lead insulating layer may have the same oxygen permeability as the measurement electrode lead or higher oxygen permeability than the measurement electrode lead. The lead insulating layer may have a porosity of, for example, 5% by volume or more and 10% by volume or less.

In the sensor element according to the present invention, the length L of the end region in the second portion is 0.25 mm or more, the length L being from the border with the first portion in the length direction of the measurement electrode lead, when viewed in the stacking direction of the plurality of solid electrolyte layers. Consequently, the above-described effect of suppressing degradation of the detection accuracy of the specific gas concentration can be more reliably ensured. In this case, the above-described length L may be 1.0 mm or more. As the length L increases, the effect of suppressing degradation of the detection accuracy of the specific gas concentration tends to be enhanced. The length L may be 1.1 mm or more.

In the sensor element according to the present invention, the length L of the end region in the second portion may be 2 mm or less, the length L being from the border with the first portion in the length direction of the measurement electrode lead, when viewed in the stacking direction of the plurality of solid electrolyte layers. Consequently, an influence by a leakage current from the measurement electrode lead can be suppressed.

In the sensor element according to the present invention, the element main body may include bonding layers that bond the solid electrolyte layers to each other, the solid electrolyte layers adjoining in the stacking direction, and the hermetic layer may be the bonding layer or be the solid electrolyte layer and the bonding layer. Consequently, a sensor element is readily produced compared with the case in which another hermetic layer different from the solid electrolyte layer or the bonding layer is used because the bonding layer can be used as the hermetic layer or the solid electrolyte layer and the bonding layer can be used as the hermetic layer.

The sensor element according to the present invention may include an outside pump electrode disposed on the outer surface of the element main body. Meanwhile, the sensor element according to the present invention may include a reference electrode disposed inside the element main body, and the element main body may include a reference gas introduction layer that introduces a reference gas into the reference electrode, the reference gas serving as the reference of detection of the specific gas concentration in the measurement-object gas. The reference gas may be the air. Meanwhile, the sensor element according to the present invention may include an inside pump electrode disposed in the flow portion of a measurement-object gas.

A gas sensor according to the present invention includes the sensor element according to any one of the above-described aspects. Consequently, the gas sensor can obtain the same effects as the above-described sensor element according to the present invention, for example, the effect of suppressing degradation of the detection accuracy of the specific gas concentration.

DETAILED DESCRIPTION OF THE INVENTION

Figure 1:
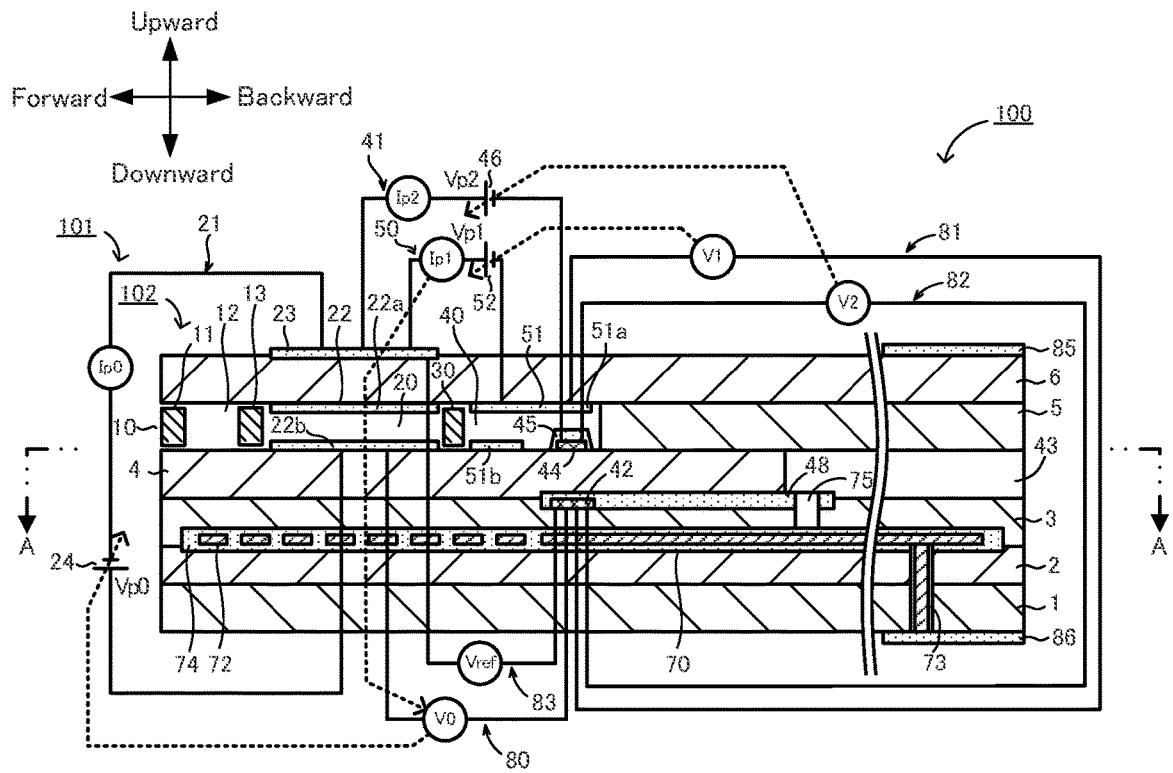
FIG. 1 is a schematic sectional view of a gas sensor 100.
Figure 2:
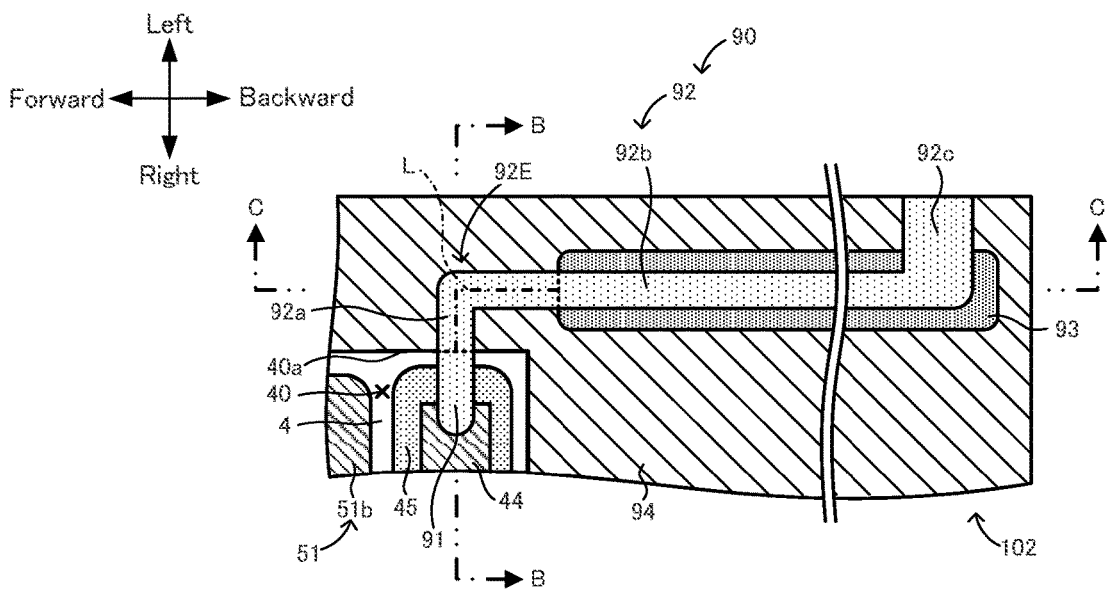
FIG. 2 is a sectional view showing part of the cross section along line A-A in FIG. 1.
Figure 3:
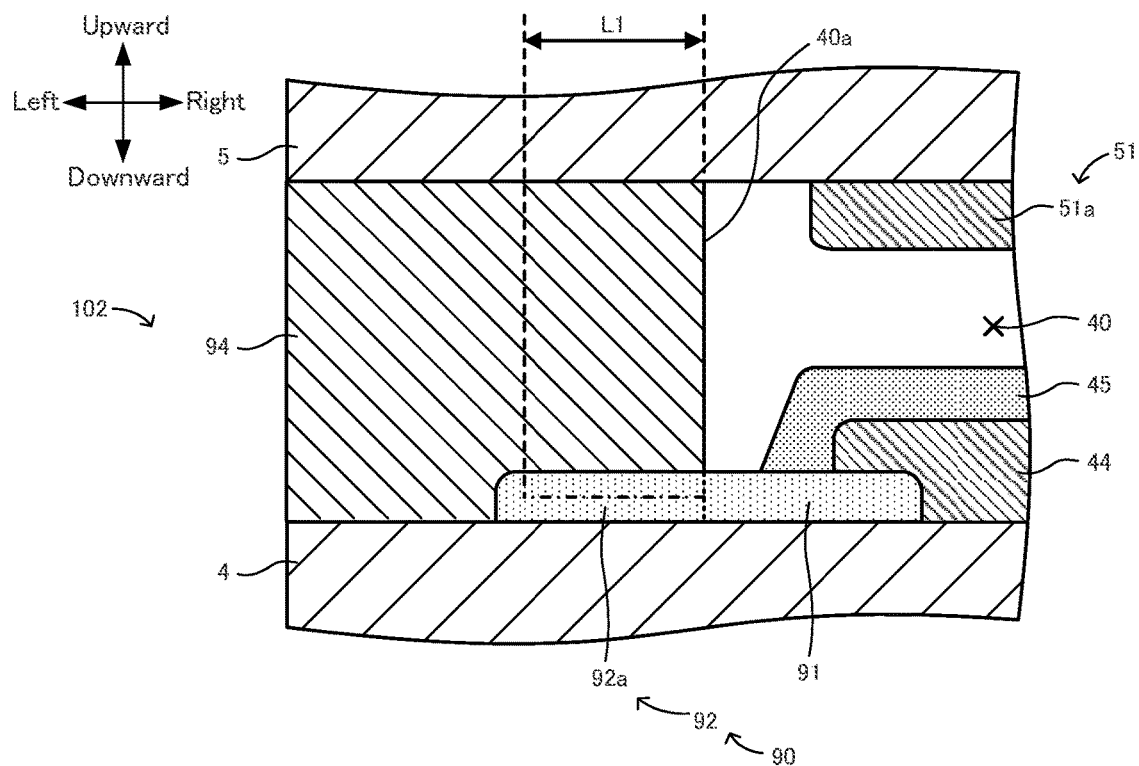
FIG. 3 is a sectional view showing the cross section along line B-B in FIG. 2.
Figure 4:
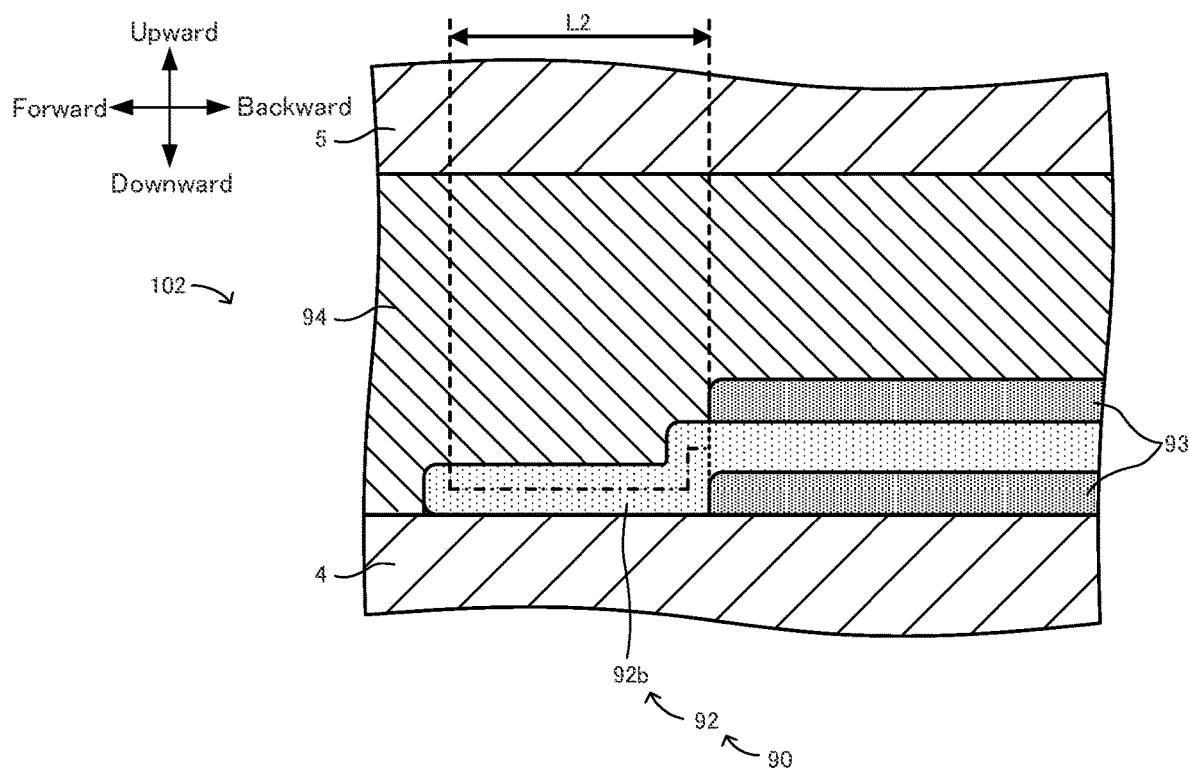
FIG. 4 is a sectional view showing part of the cross section along line C-C in FIG. 2.

Next, an embodiment according to the present invention will be described with reference to the drawings. FIG. 1 is a schematic sectional view of a gas sensor 100 including a sensor element 101 that is an embodiment of the present invention. FIG. 2 is a sectional view around a measurement electrode 44 and a measurement electrode lead 90 in the cross section along line A-A in FIG. 1. FIG. 3 is a sectional view showing the cross section along line B-B in FIG. 2. FIG. 4 is a sectional view showing part of the cross section along line C-C in FIG. 2. The gas sensor 100 includes the sensor element 101 that detects the concentration of a specific gas (NOx in the present embodiment) in a measurement-object gas. The sensor element 101 has a long rectangular parallelepiped shape, the longitudinal direction of the sensor element 101 (lateral direction in FIG. 1) is set to be the forward and backward directions, and the thickness direction of the sensor element 101 (vertical direction in FIG. 1) is set to be the vertical direction. In addition, the width direction of the sensor element 101 (direction perpendicular to the forward and backward directions and the vertical direction) is set to be the lateral direction.

The sensor element 101 is an element having a structure in which six layers of a first substrate layer 1, a second substrate layer 2, a third substrate layer 3, a first solid electrolyte layer 4, a spacer layer 5, and a second solid electrolyte layer 6 are stacked in this order from the bottom in FIG. 1, where each layer is composed of an oxygen-ion-conductive solid electrolyte layer, for example, zirconia ($ZrO_2$). In addition, the solid electrolyte for forming these six layers are dense and hermetic. The above-described sensor element 101 can be produced by, for example, subjecting ceramic green sheets corresponding to the respective layers to predetermined processing, printing of a circuit pattern, or the like, stacking the ceramic green sheets, and performing firing so as to cause integration.

A gas inlet 10, a first diffusion-controlled portion 11, a buffer space 12, a second diffusion-controlled portion 13, a first internal space 20, a third diffusion-controlled portion 30, and a second internal space 40 are successively located so as to communicate with each other in this order in one front end portion between the lower surface of the second solid electrolyte layer 6 and the upper surface of the first solid electrolyte layer 4 in the sensor element 101.

The gas inlet 10, the buffer space 12, the first internal space 20, and the second internal space 40 constitute a space located in the form of hollowing the spacer layer 5 inside the sensor element 101, where the upper portion, the lower portion, and the side portions of the space are demarcated by the lower surface of the second solid electrolyte layer 6, the upper surface of the first solid electrolyte layer 4, and the side surfaces of the spacer layer 5, respectively.

Each of the first diffusion-controlled portion 11, the second diffusion-controlled portion 13, and the third diffusion-controlled portion 30 is disposed as two landscape-oriented slits (the longitudinal direction of the opening is a direction perpendicular to the drawing). In this regard, the section from the gas inlet 10 to the second internal space 40 is also referred to as a flow portion of a measurement-object gas.

Meanwhile, a reference gas introduction space 43 is located at a location farther than the flow portion of a measurement-object gas from the front end portion and a location between the upper surface of the third substrate layer 3 and the lower surface of the spacer layer 5, where the side portions are demarcated by the side surfaces of the first solid electrolyte layer 4. For example, the air serving as the reference gas when the NOx concentration is measured is introduced into the reference gas introduction space 43.

An air introduction layer 48 is a layer composed of a porous ceramic, and the reference gas is introduced into the air introduction layer 48 through the reference gas introduction space 43. In this regard, the air introduction layer 48 is disposed so as to cover a reference electrode 42.

The reference electrode 42 is an electrode disposed in the form of being interposed between the upper surface of the third substrate layer 3 and the first solid electrolyte layer 4, and the air introduction layer 48 connected to the reference gas introduction space 43 is disposed around the reference electrode 42, as described above. Meanwhile, the oxygen concentrations (oxygen partial pressures) in the first internal space 20 and in the second internal space 40 can be measured by using the reference electrode 42, as described later.

In the flow portion of a measurement-object gas, the gas inlet 10 is a section open to the outside space, and the measurement-object gas is taken into the sensor element 101 from the outside space through the gas inlet 10. The first diffusion-controlled portion 11 is a section that provides predetermined diffusion resistance to the measurement-object gas, the gas being taken through the gas inlet 10. The buffer space 12 is a space located so as to guide the measurement-object gas, the gas being introduced from the first diffusion-controlled portion 11, to the second diffusion-controlled portion 13. The second diffusion-controlled portion 13 is a section that provides predetermined diffusion resistance to the measurement-object gas, the gas being introduced from the buffer space 12 into the first internal space 20. When the measurement-object gas is introduced from outside the sensor element 101 to inside the first internal space 20, the measurement-object gas, the gas being rapidly taken inside the sensor element 101 through the gas inlet 10 due to fluctuation of pressure (pulsation of exhaust pressure when the measurement-object gas is an automobile exhaust gas) of the measurement-object gas in the outside space, is not directly introduced into the first internal space 20 but introduced into the first internal space 20 after fluctuation of the concentration of the measurement-object gas is canceled through the first diffusion-controlled portion 11, the buffer space 12, and the second diffusion-controlled portion 13. Consequently, fluctuation of the concentration of the measurement-object gas, the gas being introduced into the first internal space 20, becomes to an extent that can be almost neglected. The first internal space 20 is disposed as a space for adjusting the oxygen partial pressure in the measurement-object gas, the gas being introduced through the second diffusion-controlled portion 13. Such an oxygen partial pressure is adjusted by an operation of the main pump cell 21.

The main pump cell 21 is an electrochemical pump cell composed of an inside pump electrode 22 having a ceiling electrode portion 22a disposed on almost entire lower surface of the second solid electrolyte layer 6 facing the first internal space 20, an outside pump electrode 23 disposed in a region corresponding to the ceiling electrode portion 22a on the upper surface of the second solid electrolyte layer 6 while being exposed to the outside space, and the second solid electrolyte layer 6 interposed between the inside pump electrode 22 and the outside pump electrode 23.

The inside pump electrode 22 is disposed so as to extend over upper and lower solid electrolyte layers (second solid electrolyte layer 6 and first solid electrolyte layer 4) that demarcate the first internal space 20 and the spacer layer 5 that provides the side walls. Specifically, the ceiling electrode portion 22a is formed on the lower surface of the second solid electrolyte layer 6 providing the ceiling surface of the first internal space 20 and a bottom electrode portion 22b is formed on the upper surface of the first solid electrolyte layer 4 providing the bottom surface. In addition, side electrode portions (not shown in the drawing) for connecting the ceiling electrode portion 22a to the bottom electrode portion 22b are formed on the side wall surfaces (inner surfaces) of the spacer layer 5 providing both side walls of the first internal space 20. Consequently, the inside pump electrode 22 is disposed so as to have a tunnel form structure in the section in which the side electrode portions are disposed.

The inside pump electrode 22 and the outside pump electrode 23 are formed as porous cermet electrodes (cermet electrodes of, for example, Pt and $ZrO_2$ containing 1% of Au). In this regard, the inside pump electrode 22 that comes into contact with the measurement-object gas is formed by using a material having a weakened ability to reduce NOx components in the measurement-object gas.

Regarding the main pump cell 21, oxygen in the first internal space 20 can be pumped to the outside space or oxygen in the outside space can be pumped into the first internal space 20 by applying a predetermined pump voltage Vp0 between the inside pump electrode 22 and the outside pump electrode 23 such that a pump current Ip0 flows between the inside pump electrode 22 and the outside pump electrode 23 in the positive direction or negative direction.

Meanwhile, in order to detect the oxygen concentration (oxygen partial pressure) in the atmosphere in the first internal space 20, the inside pump electrode 22, the second solid electrolyte layer 6, the spacer layer 5, the first solid electrolyte layer 4, the third substrate layer 3, and the reference electrode 42 constitute an electrochemical sensor cell, that is, a main pump controlling oxygen partial pressure detection sensor cell 80.

The oxygen concentration (oxygen partial pressure) in the first internal space 20 can be determined by measuring the electromotive force V0 in the main pump controlling oxygen partial pressure detection sensor cell 80. Further, the pump current Ip0 is controlled by feedback-controlling the pump voltage Vp0 of the variable power supply 24 such that the electromotive force V0 becomes constant. Consequently, the oxygen concentration in the first internal space 20 can be maintained at a predetermined constant value.

The third diffusion-controlled portion 30 is a section that provides predetermined diffusion resistance to the measurement-object gas, the gas having an oxygen concentration (oxygen partial pressure) controlled by an operation of the main pump cell 21 in the first internal space 20, and that guides the measurement-object gas to the second internal space 40.

The second internal space 40 is disposed as a space in which processing with respect to the measurement of the nitrogen oxide (NOx) concentration in the measurement-object gas, the gas being introduced through the third diffusion-controlled portion 30, is performed. Regarding the measurement of the NOx concentration, the NOx concentration is measured mainly in the second internal space 40, in which the oxygen concentration is adjusted by the auxiliary pump cell 50, by further operating a measurement pump cell 41.

In the second internal space 40, the oxygen partial pressure of the measurement-object gas, the gas being introduced through the third diffusion-controlled portion 30 after the oxygen concentration (oxygen partial pressure) has been adjusted in advance in the first internal space 20, is further adjusted by the auxiliary pump cell 50. Consequently, the oxygen concentration in the second internal space 40 can be maintained at constant with high accuracy and, therefore, the above-described gas sensor 100 can measure the NOx concentration with high accuracy.

The auxiliary pump cell 50 is an auxiliary electrochemical pump composed of the auxiliary pump electrode 51 having the ceiling electrode portion 51a disposed on almost entire lower surface of the second solid electrolyte layer 6 facing the second internal space 40, the outside pump electrode 23 (not limited to the outside pump electrode 23 as long as the electrode is an appropriate electrode outside the sensor element 101), and the second solid electrolyte layer 6.

The auxiliary pump electrode 51 is disposed in the second internal space 40 so as to have the same tunnel form structure as the above-described inside pump electrode 22 disposed in the first internal space 20. That is, regarding the tunnel form structure, the ceiling electrode portion 51a is formed on the second solid electrolyte layer 6 providing the ceiling surface of the second internal space 40, a bottom electrode portion 51b is formed on the first solid electrolyte layer 4 providing the bottom surface of the second internal space 40, and both side electrode portions (not shown in the drawing) for connecting the ceiling electrode portion 51a to the bottom electrode portion 51b are formed on the respective side wall surfaces of the spacer layer 5 providing side walls of the second internal space 40. In this regard, the auxiliary pump electrode 51 is formed by using a material having weakened ability to reduce NOx components in the measurement-object gas in the same manner as the inside pump electrode 22.

Regarding the auxiliary pump cell 50, oxygen in the atmosphere in the second internal space 40 can be pumped to the outside space or oxygen in the outside space can be pumped into the second internal space 40 by applying a predetermined pump voltage Vp1 between the auxiliary pump electrode 51 and the outside pump electrode 23.

Meanwhile, in order to control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an electrochemical sensor cell, that is, an auxiliary pump controlling oxygen partial pressure detection sensor cell 81.

In this regard, the auxiliary pump cell 50 performs pumping by a variable power supply 52 that is voltage-controlled on the basis of the electromotive force V1 detected by the auxiliary pump controlling oxygen partial pressure detection sensor cell 81. Consequently, the oxygen partial pressure in the atmosphere in the second internal space 40 is controlled to a low partial pressure that does not substantially affect the measurement of NOx.

In addition to this, the pump current Ip1 of the auxiliary pump cell 50 is used for controlling the electromotive force of the main pump controlling oxygen partial pressure detection sensor cell 80. Specifically, the pump current Ip1 serving as a control signal is input into the main pump controlling oxygen partial pressure detection sensor cell 80, the electromotive force V0 is controlled and, thereby, the gradient of the oxygen partial pressure in the measurement-object gas, the gas being introduced from the third diffusion-controlled portion 30 into the second internal space 40, is controlled so as to be always constant. In the case of application as a NOx sensor, the oxygen concentration in the second internal space 40 is maintained at a constant value of about 0.001 ppm by the functions of the main pump cell 21 and the auxiliary pump cell 50.

The measurement pump cell 41 measures the NOx concentration in the measurement-object gas in the second internal space 40. The measurement pump cell 41 is an electrochemical pump cell constructed by a measurement electrode 44 disposed on the upper surface of the first solid electrolyte layer 4 facing the second internal space 40 and at the position apart from the third diffusion-controlled portion 30, the outside pump electrode 23, the second solid electrolyte layer 6, the spacer layer 5, and the first solid electrolyte layer 4.

The measurement electrode 44 is a porous cermet electrode. The measurement electrode 44 also functions as a NOx reduction catalyst for reducing NOx present in the atmosphere in the second internal space 40. Further, the measurement electrode 44 is covered with a fourth diffusion-controlled portion 45.

The fourth diffusion-controlled portion 45 is a film composed of a ceramic porous body. The fourth diffusion-controlled portion 45 has a function of restricting the amount of NOx that flows into the measurement electrode 44 and, in addition, a function as a protective film for the measurement electrode 44. In the measurement pump cell 41, oxygen generated by decomposition of nitrogen oxides in the atmosphere around the measurement electrode 44 is pumped out and the amount of the oxygen generated can be detected as a pump current Ip2.

Meanwhile, in order to detect the oxygen partial pressure around the measurement electrode 44, an electrochemical sensor cell, that is, a measurement pump controlling oxygen partial pressure detection sensor cell 82 is constructed by the first solid electrolyte layer 4, the third substrate layer 3, the measurement electrode 44, and the reference electrode 42. A variable power supply 46 is controlled on the basis of the electromotive force V2 detected by the measurement pump controlling oxygen partial pressure detection sensor cell 82.

The measurement-object gas, the gas being introduced into the second internal space 40, reaches the measurement electrode 44 through the fourth diffusion-controlled portion 45 under circumstances where the oxygen partial pressure is controlled. Nitrogen oxides in the measurement-object gas around the measurement electrode 44 are reduced ($2NO \rightarrow N_2 + O_2$) and oxygen is generated. Then, the resulting oxygen is pumped by the measurement pump cell 41. At this time, the voltage Vp2 of the variable power supply 46 is controlled so as to make the electromotive force V2 detected by the measurement pump controlling oxygen partial pressure detection sensor cell 82 constant. The amount of oxygen generated around the measurement electrode 44 is proportional to the concentration of the nitrogen oxides in the measurement-object gas and, therefore, the nitrogen oxide concentration in the measurement-object gas is calculated by using the pump current Ip2 of the measurement pump cell 41.

In addition, when the measurement electrode 44, the first solid electrolyte layer 4, the third substrate layer 3, and the reference electrode 42 are combined so as to constitute an oxygen partial pressure detection device as an electrochemical sensor cell, the electromotive force in accordance with the difference between the amount of oxygen generated by reduction of NOx components in the atmosphere around the measurement electrode 44 and the amount of oxygen contained in the reference air can be detected and, thereby, the concentration of NOx components in the measurement-object gas can be determined.

Further, an electrochemical sensor cell 83 is constructed by the second solid electrolyte layer 6, the spacer layer 5, the first solid electrolyte layer 4, the third substrate layer 3, the outside pump electrode 23, and the reference electrode 42. The oxygen partial pressure in the measurement-object gas outside the sensor can be detected by the electromotive force Vref obtained by the sensor cell 83.

In the gas sensor 100 having the above-described configuration, the measurement-object gas that has an oxygen partial pressure always maintained at a low constant value (value that does not substantially affect the measurement of NOx) by actuation of the main pump cell 21 and the auxiliary pump cell 50 is fed to the measurement pump cell 41. Therefore, the NOx concentration in the measurement-object gas can be determined on the basis of the pump current Ip2 that flows because of oxygen generated by reduction of NOx nearly in proportion to the NOx concentration in the measurement-object gas being pumped out by the measurement pump cell 41.

Further, in order to enhance the oxygen ion conductivity of the solid electrolyte, the sensor element 101 includes a heater portion 70 having a function of performing temperature adjustment that includes heating the sensor element 101 and keeping the temperature. The heater portion 70 includes a heater 72, a through hole 73, a heater insulating layer 74, and a pressure release hole 75.

The heater 72 is an electric resistor formed to be interposed between the second substrate layer 2 and the third substrate layer 3 in the vertical direction. The heater 72 is connected to a lower connector pad 86 via the through hole 73 and generates heat by being supplied with an electric power from the outside through the lower connector pad 86 so as to heat the solid electrolyte constituting the sensor element 101 and keep the temperature.

Meanwhile, the heater 72 is embedded over an entire range from the first internal space 20 to the second internal space 40, and the entirety of the sensor element 101 can be adjusted to have a temperature at which the above-described solid electrolyte is activated.

The heater insulating layer 74 is an insulating layer formed on the upper and lower surfaces of the heater 72 by using an insulator, for example, alumina. The heater insulating layer 74 is formed for the purpose of establishing electrical insulation between the second substrate layer 2 and the heater 72 and electrical insulation between the third substrate layer 3 and the heater 72.

The pressure release hole 75 is a section located so as to pass through the third substrate layer 3 and to communicate with the reference gas introduction space 43 and is formed for the purpose of reducing an internal pressure increase associated with a temperature increase in the heater insulating layer 74.

An upper connector pad 85 is disposed on the rear end portion of the upper surface of the second solid electrolyte layer 6 (refer to FIG. 1). Likewise, the lower connector pad 86 is disposed on the rear end portion of the lower surface of the first substrate layer 1. The upper connector pad 85 and the lower connector pad 86 function as connector electrodes that electrically connect the sensor element 101 to the outside. A plurality of upper connector pads 85 and a plurality of lower connector pads 86 (four each in the present embodiment) are disposed, although not shown in the drawing. One of the upper connector pads 85 is connected to the measurement electrode lead 90 shown in FIGS. 2 to 4 and is connected to the measurement electrode 44 via the measurement electrode lead 90. Each of the electrodes other than the measurement electrode 44 is connected to any one of the upper connector pads 85 and the lower connector pads 86 via an electrode lead, although not shown in the drawing. A voltage or a current can be applied from the outside to each electrode (inside pump electrode 22, outside pump electrode 23, reference electrode 42, measurement electrode 44, and auxiliary pump electrode 51) of the sensor element 101 or the voltage or the current of each electrode can be measured via the upper connector pads 85 or the lower connector pads 86. In practice, the application of the voltage by the variable power supply 24, the variable power supply 46, and the variable power supply 52 and the detection of the pump currents Ip0, Ip1, and Ip2, electromotive forces V0, V1, V2, and Vref, and the like are performed via the upper connector pads 85 and the lower connector pads 86.

Meanwhile, as shown in FIGS. 2 to 4, although not shown in FIG. 1, a hermetic bonding layer 94 is present on the first solid electrolyte layer 4. The bonding layer 94 bonds the first solid electrolyte layer 4 to the spacer layer 5 that are adjacent to each other in the stacking direction of the layers 1 to 6 (here, vertical direction). The bonding layer 94 covers almost entire upper surface of the first solid electrolyte layer 4 excluding the flow portion of a measurement-object gas, for example, the buffer space 12, the first internal space 20, and the second internal space 40. It is preferable that the bonding layer 94 have oxygen-ion conductivity in the same manner as each of the layers 1 to 6. In the present embodiment, the bonding layer 94 is set to be a ceramic containing zirconia as a primary component in the same manner as each of the layers 1 to 6. In addition, although not shown in the drawing, the bonding layer is present not only between the spacer layer 5 and the first solid electrolyte layer 4 but also between the layers, which are adjacent to each other in the stacking direction, of the layers 1 to 6.

In this regard, in the sensor element 101, the layers 1 to 6, the bonding layers between the layers including the bonding layer 94, and the like are referred to as an element main body 102. The element main body 102 does not include spaces (flow portion of a measurement-object gas, reference gas introduction space 43, and pressure release hole 75) nor constitute elements (electrodes, electrode leads, upper connector pads 85, lower connector pads 86, and heater 72) that are energized.

The configuration of and around the measurement electrode lead 90 will be described with reference to FIGS. 2 to 4. As shown in FIG. 2, the measurement electrode lead 90 is arranged to the left of the measurement electrode 44 in the sensor element 101. The measurement electrode lead 90 has a first portion 91 that is connected to the measurement electrode 44 and that is disposed in the second internal space 40 in the flow portion of a measurement-object gas and a second portion 92 that is connected to the left of the first portion 91 and that is embedded in the element main body 102 of the sensor element 101. As shown in FIGS. 2 and 3, the first portion 91 is a portion from the part connected to the measurement electrode 44 to a left side surface 40a of the second internal space 40 in the measurement electrode lead 90. The first portion 91 has a linear shape. The first portion 91 is disposed directly on the upper surface of the first solid electrolyte layer 4. Part of the first portion 91 is exposed to the second internal space 40 and the other part is covered with the measurement electrode 44 and the fourth diffusion-controlled portion 45. The second portion 92 has a first linear portion 92a to a third linear portion 92c. The first linear portion 92a is disposed in the lateral direction while the right end is connected to the left end portion of the first portion 91. The second linear portion 92b is disposed in the forward and backward directions and extends to the vicinity of the rear end of the sensor element 101 while the front end is connected to the left end portion of the first linear portion 92a. The third linear portion 92c is disposed in the lateral direction and extends to the left end of the sensor element 101 while the right end is connected to the rear end portion of the second linear portion 92b. The left end portion of the third linear portion 92c is exposed at the left side surface of the sensor element 101 and is connected to one of the upper connector pads 85 via the side surface lead, although not shown in the drawing. The border between the first portion 91 and the second portion 92 is flush with the left side surface 40a of the second internal space 40. The measurement electrode lead 90 is, for example, a cermet conductor containing a noble metal such as platinum or a high-melting-point metal such as tungsten or molybdenum and containing zirconia that is the same as the primary component of the first solid electrolyte layer 4. The measurement electrode lead 90 is hermetic and hardly passes oxygen. The measurement electrode lead 90 may have a porosity of, for example, 0% by volume or more and 10% by volume or less. The measurement electrode lead 90 has a porosity of preferably less than 5% by volume and more preferably 2% by volume or less.

Part of the measurement electrode lead 90 is surrounded by the lead insulating layer 93. Meanwhile, the end region 92E (refer to FIG. 2) that is part of the second portion 92 is not surrounded by the lead insulating layer 93. In the second portion 92, the end region 92E is an end region that adjoin the first portion 91 and that includes the border with the first portion 91. In the present embodiment, the end region 92E includes the entire first linear portion 92a and a front part of the second linear portion 92b. When the end region 92E is viewed in the stacking direction of the element main body 102 (here, vertical direction), the length of the second portion 92 from the border with the first portion 91 in the length direction of the measurement electrode lead 90 is denoted as a length L. The length direction of the measurement electrode lead 90 is the axis direction of the center axis of the measurement electrode lead 90 and is the flow direction of a current that flows through the measurement electrode lead 90. In FIG. 2, the length of the bent line segment indicated by alternate long and short dashed lines in the end region 92E is the length L. Meanwhile, the total of a length L1 of the first linear portion 92a shown in FIG. 3 and a length L2 shown in FIG. 4 is the length L. In this regard, the length L1 in FIG. 3 is the length from the left side surface 40a to the center axis of the second linear portion 92b in the lateral direction of the first linear portion 92a in top view. The length L2 in FIG. 4 is the length from the center axis of the first linear portion 92a to the front end of the lead insulating layer 93 in the forward and backward directions of the second linear portion 92b in top view. In this regard, as shown in FIG. 4, the end region 92E is disposed directly on the first solid electrolyte layer 4, and in the second linear portion 92b, the portion other than the end region 92E is disposed on the lead insulating layer 93. Consequently, in the end region 92E, the vicinity of the end portion adjoining the lead insulating layer 93 has a step with a vertical height difference. However, as described above, the length L is the length when viewed in the stacking direction.

Therefore, regarding the value of the length L, the value of such a height difference in the stacking direction is not taken into consideration. The length L is preferably 0.25 mm or more, more preferably 1.0 mm or more, and further preferably 1.1 mm or more (the reason will be described later). In addition, the length L is preferably 2 mm or less. The first solid electrolyte layer 4 is present under the end region 92E, and the bonding layer 94 is present on the top, the front, the rear, and either side of the end region 92E. Therefore, the end region 92E is interposed between the first solid electrolyte layer 4 and the bonding layer 94 and surrounded by these. The first solid electrolyte layer 4 and the bonding layer 94 are hermetic, as described above, and these correspond to the hermetic layers according to the present invention. In this regard, the porosity of the hermetic layer (here, the first solid electrolyte layer 4 and the bonding layer 94) may be, for example, 0% by volume or more and 2% by volume or less. The porosity of the first solid electrolyte layer 4 may be 0% by volume or more and 2% by volume or less. The porosity of the bonding layer 94 may be 0% by volume or more and 2% by volume or less.

The lead insulating layer 93 is part of the element main body 102 and surrounds at least part of a portion excluding the end region 92E of the second portion 92 of the measurement electrode lead 90 so as to insulate the portion from the first solid electrolyte layer 4 and the spacer layer 5. The lead insulating layer 93 is disposed such that the longitudinal direction is in accord with the forward and backward directions. The lead insulating layer 93 surrounds the top, the bottom, and either side of a portion excluding the end region 92E of the second linear portion 92b. In addition, the lead insulating layer 93 surrounds the top, the bottom, the front, and the rear of a portion excluding the vicinity of the left end portion of the sensor element 101 of the third linear portion 92c. That is, the lead insulating layer 93 surrounds the entire second portion 92 excluding the end region 92E and the region including the end portion opposite to the end region 92E. In this regard, the lead insulating layer 93 does not surround the first portion 91 nor the left end portion of the third linear portion 92c. Consequently, the lead insulating layer 93 is suppressed from covering portions, for example, the connection portion between the first portion 91 and the measurement electrode 44 and the left end portion of the third linear portion 92c, that have to be electrically connected during production of the sensor element 101. The lead insulating layer 93 is a ceramic insulator, for example, alumina. The lead insulating layer 93 has a higher oxygen permeability than the hermetic layer (here, the first solid electrolyte layer 4 and the bonding layer 94). The lead insulating layer 93 has the oxygen permeability higher than or equal to the oxygen permeability of the measurement electrode lead 90. The porosity of the lead insulating layer 93 may be, for example, 5% by volume or more and 10% by volume or less. The lead insulating layer 93 is interposed between the first solid electrolyte layer 4 and the bonding layer 94 and surrounded by these. Meanwhile, the minimum distance between the lead insulating layer 93 and the flow portion of a measurement-object gas (here, the second internal space 40) may be 0.25 mm or more or be 0.3 mm or more. In FIG. 2, the minimum distance between the lead insulating layer 93 and the second internal space 40 is the distance between the front right end portion of the lead insulating layer 93 and the rear left end portion of the second internal space 40.

Next, an example of the method for manufacturing the above-described gas sensor 100 will be described. Initially, six unfired ceramic green sheets containing an oxygen-ion-conductive solid electrolyte, for example, zirconia, as a ceramic component are prepared. A plurality of sheet holes used for registration during printing and stacking, necessary through holes, and the like are located in advance in the green sheets. In addition, a space serving as the flow portion of a measurement-object gas is located in the green sheet serving as the spacer layer 5 by stamping treatment or the like in advance. Subsequently, pattern printing treatment in which various patterns are formed on the ceramic green sheets in accordance with each of the first substrate layer 1, the second substrate layer 2, the third substrate layer 3, the first solid electrolyte layer 4, the spacer layer 5, and the second solid electrolyte layer 6 and drying treatment are performed. Specifically, the patterns formed are patterns of, for example, electrodes of the above-described measurement electrode 44 and the like, lead wires such as the measurement electrode lead 90 to be connected to electrodes, the lead insulating layer 93, the upper connector pads 85, the lower connector pads 86, the air introduction layer 48, and the heater portion 70. Pattern printing is performed by coating the green sheets with pattern-forming pastes prepared in accordance with the characteristics required for the respective objects to be formed by using a known screen printing technology. The drying treatment is also performed by using a known drying device. After pattern printing and drying are finished, printing and drying treatments of a bonding paste serving as the bonding layers for bonding green sheets corresponding to the respective layers to each other are performed. Then, the green sheets provided with the bonding pastes are registered by sheet holes and stacked in the predetermined order, and contact bonding treatment is performed so as to produce a single multilayer body by causing contact bonding under predetermined temperature and pressure conditions. The thus obtained multilayer body includes a plurality of sensor elements 101. The resulting multilayer body is cut and divided into the size of a sensor element 101. The divided multilayer body is fired at a predetermined firing temperature so as to obtain the sensor element 101.

In this regard, patterns serving as the measurement electrode lead 90 and the lead insulating layer 93 may be formed on the green sheet serving as the first solid electrolyte layer 4 as described below, for example. Initially, a pattern serving as a portion that covers the lower part of the measurement electrode lead 90 of the lead insulating layer 93 is formed on the green sheet. Subsequently, a pattern serving as the measurement electrode lead 90 is formed. Then, a portion that covers the side part and the upper part of the measurement electrode lead 90 of the lead insulating layer 93 is formed. In this regard, the pattern serving as the measurement electrode lead 90 may be formed in a plurality of batches.

Thereafter, the gas sensor 100 incorporated with the sensor element 101 is produced. For example, an element sealing body is attached to the sensor element 101 so as to perform sealing and fixing, and connectors and lead wires are attached to the rear end of the sensor element 101 so as to be electrically connected to the upper connector pads 85 or the lower connector pads 86. Meanwhile, a protective cover is attached to the element sealing body on the front end of the sensor element 101. In addition, an outer cylinder is attached to the element sealing body on the rear end of the sensor element 101 while the lead wire extends from the outer cylinder. In this regard, the steps of assembling the gas sensor 100 incorporated with such a sensor element 101 have been known and are described in, for example, JP 2015-178988 A.

Figure 5:
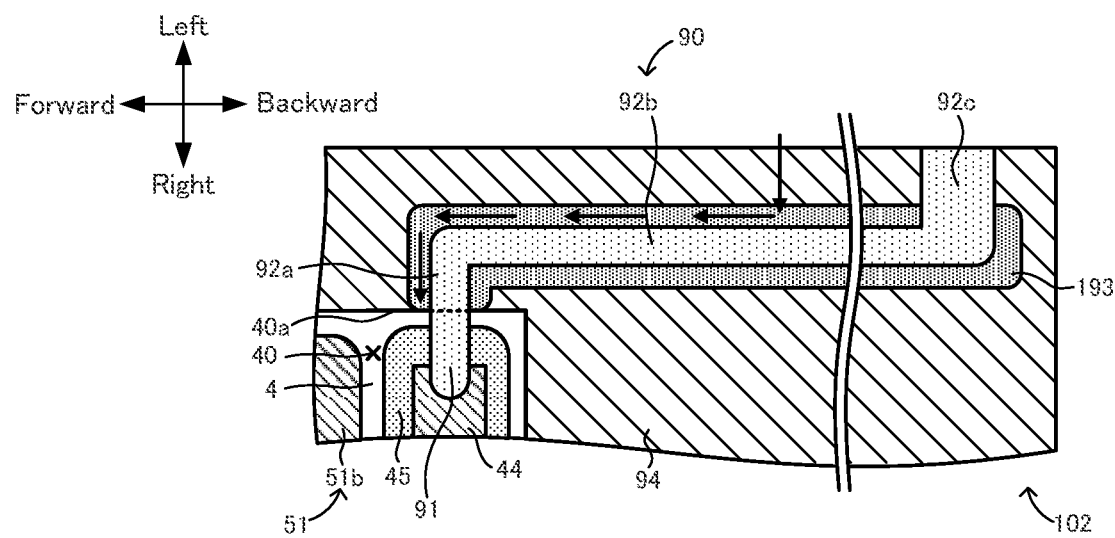
FIG. 5 is a sectional view showing a lead insulating layer 193 of a comparative example.

Here, the reason for the end region 92E of the measurement electrode lead 90 being surrounded by the hermetic layer (first solid electrolyte layer 4 and bonding layer 94) in the gas sensor 100 will be described. In the sensor element 101, paths through which oxygen reaches the lead insulating layer 93 from the outside may be present. Such paths may be formed due to, for example, dust that intrudes during production of the sensor element or cracks after production. If such paths are present, oxygen (for example, the air containing oxygen) may reach the lead insulating layer 93 from outside the sensor element 101, and the oxygen may further moves in the lead insulating layer 93. Then, if such oxygen reaches the second internal space 40, oxygen that is not derived from NOx increases around the measurement electrode 44, and the detection accuracy of the NOx concentration is degraded. For example, if oxygen that is not derived from NOx increases, the pump current Ip2 and the electromotive force V2 shown in FIG. 1 are changed, and when the NOx concentration is detected by using at least one of these, the detection accuracy is degraded. However, in the gas sensor 100 according to the present embodiment, the end region 92E is not surrounded by the lead insulating layer 93 that passes oxygen but is surrounded by the hermetic layer (first solid electrolyte layer 4 and bonding layer 94) that hardly passes oxygen instead. When the end region 92E that is a portion serving as the outlet to the second internal space 40 in the second portion 92 of the measurement electrode lead 90 is surrounded by the hermetic layer, as described above, oxygen in the lead insulating layer 93 does not readily reach the second internal space 40. Consequently, oxygen from the outside does not readily reach the measurement electrode 44, and the above-described degradation of the detection accuracy of the NOx concentration can be suppressed. Meanwhile, for example, the case in which a lead insulating layer 193 surrounds the portion corresponding to the end region 92E and is exposed at the left side surface 40a (corresponding to the case in which the length L=0), as in the comparative example shown in FIG. 5, is considered. In this comparative example, the above-described degradation of the detection accuracy of the NOx concentration readily occurs because oxygen readily reaches the second internal space 40 through the lead insulating layer 93 as indicated by arrows.

In this regard, in the comparative example shown in FIG. 5, even when no path from the outside to the lead insulating layer 93 is present, oxygen (for example, the air containing oxygen) may move from the flow portion of a measurement-object gas into the lead insulating layer 93 during no use of the sensor element 101. In this case, the detection accuracy of the NOx concentration may be degraded because oxygen in the lead insulating layer 93 is fed into the second internal space 40 during use of the sensor element 101. The detection accuracy is recovered by the auxiliary pump cell 50 performing pumping such that the oxygen fed from the lead insulating layer 93 is pumped to the outside. However, the detection accuracy is in a degraded state during at least a period in which pumping is insufficient, for example, when use of the sensor element 101 is started. As a result, in the comparative example shown in FIG. 5, it may take a time until the signal of the sensor element 101 (for example, pump current Ip2) is stabilized at a value indicating a correct NOx concentration. On the other hand, in the gas sensor 100 according to the present embodiment, the hermetic layer surrounds the end region 92E of the measurement electrode lead 90, and oxygen in the lead insulating layer 93 is not readily fed to the second internal space 40. Therefore, the time period from the start of use of the sensor element 101 until stabilization of the signal can be reduced. As described above, regarding the gas sensor 100 according to the present embodiment, degradation of the detection accuracy of the NOx concentration in the case in which paths of oxygen from the outside are present can be suppressed and, further, the time required for stabilizing the signal of the sensor element 101 can be reduced.

According to the gas sensor 100 of the present embodiment described above in detail, the hermetic layer surrounds the end region 92E of the measurement electrode lead 90 and, therefore, degradation of the detection accuracy of the NOx concentration due to oxygen from the outside reaching the measurement electrode 44 can be suppressed. In addition, such an effect of suppressing the degradation of the detection accuracy of the NOx concentration is more reliably obtained by setting the length L to be 0.25 mm or more. In this regard, as the length L increases, such an effect of suppressing the degradation of the detection accuracy of the NOx concentration tends to be enhanced.

In addition, when the length L of the end region 92E is 2 mm or less, an influence of a leakage current from the measurement electrode lead 90 can be suppressed.

Further, the element main body 102 includes the bonding layer 94 that bonds the first solid electrolyte layer 4 to the spacer 5 adjacent to each other in the stacking direction, and the hermetic layer surrounding the end region 92E is the first solid electrolyte layer 4 and the bonding layer 94. Therefore, the first solid electrolyte layer 4 and the bonding layer 94 can be used as the hermetic layer and, as a result, the sensor element 101 can readily be produced compared with the case in which the end region 92E is surrounded by using another hermetic layer different from the first solid electrolyte layer 4 or the bonding layer 94.

Note that, needless to say, the present invention is not limited to the above-described embodiment and can be realized in various forms within the technical scope of the present invention.

For example, in the above-described embodiment, the end region 92E includes the entire first linear portion 92a and the front part of the second linear portion 92b, but the end region 92E is not limited to this. For example, the end region 92E may be only part of the first linear portion 92a. Meanwhile, the shape of the measurement electrode lead 90 (path of lead wire) is not limited to the above-described embodiment. For example, in the above-described embodiment, the border between the first portion 91 and the second portion 92 is set to be the left side surface 40a of the second internal space 40, but the border is not limited to this. The border may be the right side surface or the rear side surface of the second internal space 40.

In the above-described embodiment, the hermetic layer surrounding the end region 92E is set to be the first solid electrolyte layer 4 and the bonding layer 94, but the hermetic layer is not limited to this. For example, the bonding layer 94 may also be present under the end region 92E, and the end region 92E may be surrounded by the bonding layer 94. That is, the hermetic layer may be the bonding layer 94. Alternatively, the hermetic layer surrounding the end region 92E may be another hermetic member different from the first solid electrolyte layer 4 or the bonding layer 94.

In the above-described embodiment, the lead insulating layer 93 surrounds the entire second portion 92 excluding the end region 92E and the region including the end portion opposite to the end region 92E, but the lead insulating layer 93 is not limited to this. The lead insulating layer 93 may surround at least part of the second portion 92 excluding the end region 92E.

Figure 6:
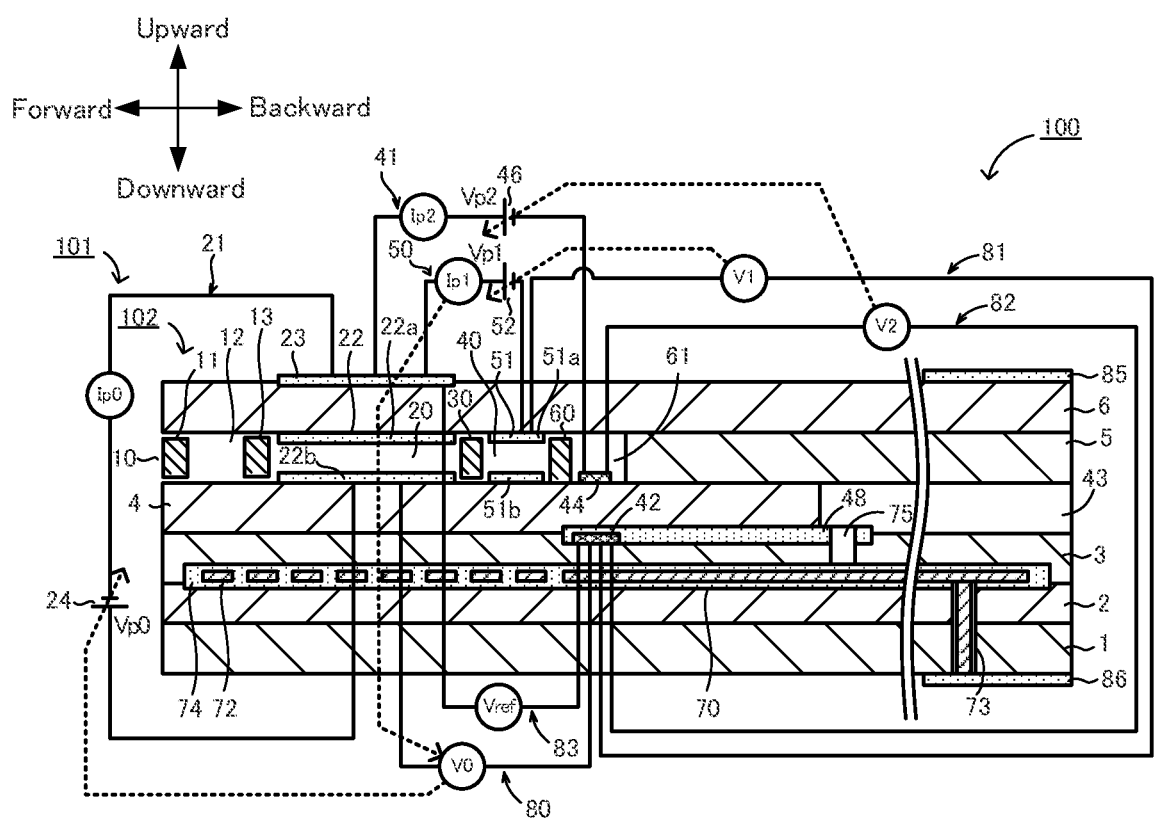
FIG. 6 is a schematic sectional view of a gas sensor 100 of a modified example.

In the above-described embodiment, the sensor element 101 of the gas sensor 100 is set to include the first internal space 20 and the second internal space 40, but the sensor element 101 is not limited to this. For example, a third internal space may be further included. FIG. 6 is a schematic sectional view of the gas sensor 100 of a modified example in this case. As shown in FIG. 6, in the gas sensor 100 of this modified example, the measurement electrode 44 is not covered with the fourth diffusion-controlled portion 45. A fourth diffusion-controlled portion 60 similar to the third diffusion-controlled portion 30 is disposed instead between the auxiliary pump electrode 51 and the measurement electrode 44. Consequently, the second internal space 40, the fourth diffusion-controlled portion 60, and the third internal space 61 are successively located so as to communicate with each other in this order and constitute part of the flow portion of a measurement-object gas. In this regard, the auxiliary pump electrode 51 is disposed in the second internal space 40, and the measurement electrode 44 is disposed on the upper surface of the first solid electrolyte layer 4 facing the third internal space 61. The gas sensor 100 of the modified example can detect the NOx concentration in the measurement-object gas in the same manner as the above-described embodiment because the fourth diffusion-controlled portion 60 has the same function as the fourth diffusion-controlled portion 45 in FIG. 1. In addition, regarding the gas sensor 100 of the modified example, in the same manner as the above-described embodiment, the hermetic layer surrounds the end region of the measurement electrode lead and, thereby, degradation of the detection accuracy of the NOx concentration due to oxygen from the outside reaching the measurement electrode 44 can be suppressed.

In the above-described embodiment, the voltage Vp2 of the variable power supply 46 is controlled such that the electromotive force V2 becomes constant, and the NOx concentration in the measurement-object gas is calculated by using the pump current Ip2 at this time. However, the configuration is not limited to this as long as a specific concentration in the measurement-object gas is detected on the basis of the voltage between the reference electrode 42 and the measurement electrode 44. For example, when an oxygen partial pressure detection device is constructed as an electrochemical cell by combining the measurement electrode 44, the first solid electrolyte layer 4, the third substrate layer 3, and the reference electrode 42, an electromotive force in accordance with the difference between the amount of oxygen generated by reduction of NOx components in the atmosphere around the measurement electrode 44 and the amount of oxygen contained in the reference gas can be detected, and as a result, the concentration of the NOx components in the measurement-object gas can be determined. In this regard, in the same manner as the above-described embodiment, the hermetic layer surrounds the end region of the measurement electrode lead and, thereby, degradation of the detection accuracy of the NOx concentration due to oxygen from the outside reaching the measurement electrode 44 can be suppressed.

In the above-described embodiment, the sensor element 101 detects the NOx concentration as the specific gas concentration in the measurement-object gas, but the specific gas concentration is not limited to this. For example, the sensor element 101 may detect an oxygen concentration as the specific gas concentration.

EXAMPLES

Instances in which the sensor elements are specifically produced will be described below as examples. In this regard, the present invention is not limited to the following examples.

Example 1

In example 1, the sensor element 101 illustrated in FIGS. 1 to 4 was formed following the above-described method for manufacturing the sensor element 101. When producing the sensor element 101, ceramic green sheets serving as the layers 1 to 6 were prepared by mixing zirconia particles containing 4% by mole of yttria serving as a stabilizer, an organic binder, and an organic solvent and performing tape forming. A paste for forming the measurement electrode lead 90 was prepared by mixing 11.2% by mass of zirconia particles containing 4% by mole of yttria serving as a stabilizer, 60% by mass of platinum, the organic binder, and the organic solvent. A paste for forming the lead insulating layer 93 was prepared by mixing an alumina powder and a binder solution at a weight ratio of 1:2. A paste for forming the bonding layer 94 was prepared by mixing zirconia particles containing 4% by mole of yttria serving as a stabilizer, the organic binder, and the organic solvent. In the sensor element 101, the length L of the end region 92E of the measurement electrode lead 90 was set to be 1.1 mm. The lead insulating layer 93 had a higher porosity than the first solid electrolyte layer 4, the bonding layer 94, and the measurement electrode lead 90. Consequently, it is conjectured that the lead insulating layer 93 has a higher oxygen permeability than the first solid electrolyte layer 4, the bonding layer 94, and the measurement electrode lead 90.

Example 2

In example 2, the sensor element 101 was produced in the same manner as example 1 except that the length L was set to be 0.25 mm. In this regard, in example 2, the end region 92E was set to be only part of the first linear portion 92a.

Comparative Example 1

In comparative example 1, the sensor element 101 was produced in the same manner as example 1 except that the pattern of the lead insulating layer 193 was formed while the length L was set to be 0 mm, as shown in FIG. 5.

[Evaluation of Detection Accuracy]

Regarding each of examples 1 and 2 and comparative example 1, the detection accuracy of the measurement-object gas of the sensor element 101 was evaluated. In this regard, in evaluation of the detection accuracy, paths of oxygen from the outside to the lead insulating layer 93 were intentionally formed by arranging foreign matters such as hairs and fibers of clothing between the green sheets serving as the first solid electrolyte layer 4 and the spacer 5 before the layers were stacked during production in examples 1 and 2 and comparative example 1. Subsequently, regarding each of examples 1 and 2 and comparative example 1 after production, the detection accuracy was evaluated. Specifically, the sensor element 101 was arranged in the air initially, and the heater 72 was energized by applying a voltage to the heater portion 70 such that the temperature of the heater 72 became a predetermined temperature. Meanwhile, a model gas in which the base gas was nitrogen, the oxygen concentration was 18%, and the NOx concentration was 0 ppm was introduced into the gas flow portion. Subsequently, each of cells 21, 41, 50, and 80 to 83 was driven. After the value of the pump current Ip2 was stabilized, the resulting value of the pump current Ip2 was measured. Then, the case in which the value of the pump current Ip2 was within an allowable range (0 µA or more and 1 µA or less) when the oxygen concentration was 18% was rated as good (A), and the case in which the value was out of the allowable range was rated as faulty (F). The value of the length L and the result of rating of each of examples 1 and 2 and comparative example 1 are shown in Table 1.

TABLE 1

|  | Length L [mm] | Evaluation of Detection Accuracy |
|---|---|---|
| Example 1 | 1.1 | A |
| Example 2 | 0.25 | A |
| Comparative Example 1 | 0 | F |

As shown in Table 1, regarding comparative example 1 in which the length L was 0 mm, the evaluation result of the detection accuracy was faulty, whereas the evaluation results of the detection accuracy of examples 1 and 2 in which the length L was 0.25 mm or more were good. In this regard, in comparative example 1, the value of the pump current Ip2 was more than the allowable range. As oxygen around the measurement electrode 44 increases, the pump current Ip2 tends to increase. Therefore, it is conjectured that regarding comparative example 1, oxygen in the model gas reached the second internal space 40 from the outside and, thereby, the value of the pump current Ip2 became the large value.

What is claimed is:

1. A sensor element comprising:
    an element main body which has a plurality of oxygen-ion-conductive solid electrolyte layers stacked and in which a flow portion of a measurement-object gas is disposed so as to introduce and pass the measurement-object gas;
    a measurement electrode disposed in the flow portion of the measurement-object gas;
    a measurement electrode lead having a first portion that is connected to the measurement electrode and that is disposed in the flow portion of the measurement-object gas and a second portion that is connected to the first portion and that is embedded in the element main body;
    a hermetic layer that is part of the element main body and that surrounds an end region of the second portion including a border with the first portion; and
    a lead insulating layer that is part of the element main body and that surrounds at least part of the second portion excluding the end region,
    wherein a length L of the end region in the second portion is 0.25 mm or more, the length L being from the border with the first portion to a front end of the lead insulating layer in a length direction of the measurement electrode lead, when viewed in a stacking direction of the plurality of solid electrolyte layers, and
    wherein the length L is 2 mm or less.

2. The sensor element according to claim 1, wherein the length L is 1.0 mm or more.

3. The sensor element according to claim 1, wherein the element main body includes bonding layers that bond the plurality of solid electrolyte layers to each other, the plurality of solid electrolyte layers adjoining in the stacking direction, and
    the hermetic layer is one of the bonding layers or is one of the plurality of solid electrolyte layers and one of the bonding layers.

4. A gas sensor comprising the sensor element according to claim 1.

* * * * *